(12) United States Patent
Kirson et al.

(10) Patent No.: US 11,452,863 B2
(45) Date of Patent: Sep. 27, 2022

(54) ARRAYS FOR LONGITUDINAL DELIVERY OF TTFIELDS TO A BODY

(71) Applicant: Novocure GmbH, Root (CH)

(72) Inventors: Eilon Kirson, Ramat Hasharon (IL); Yoram Wasserman, Haifa (IL); Hadas Sara Hershkovich, Kiryat Motzkin (IL); Zeev Bomzon, Kiryat Tivon (IL)

(73) Assignee: Novocure GmbH, Root (CH)

( * ) Notice: Subject to any disclaimer, the term of this patent is extended or adjusted under 35 U.S.C. 154(b) by 308 days.

(21) Appl. No.: 16/560,306

(22) Filed: Sep. 4, 2019

(65) Prior Publication Data
US 2020/0001069 A1   Jan. 2, 2020

Related U.S. Application Data

(63) Continuation of application No. 15/636,722, filed on Jun. 29, 2017, now Pat. No. 10,441,776.
(Continued)

(51) Int. Cl.
*A61N 1/04* (2006.01)
*A61N 1/40* (2006.01)
(Continued)

(52) U.S. Cl.
CPC ........ *A61N 1/0476* (2013.01); *A61K 41/0052* (2013.01); *A61N 1/044* (2013.01);
(Continued)

(58) Field of Classification Search
CPC ...... A61N 1/0476; A61N 1/044; A61N 1/321; A61N 1/0408; A61N 1/40; A61N 1/0484
See application file for complete search history.

(56) References Cited

U.S. PATENT DOCUMENTS 7,146,210 B2   12/2006 Palti
7,565,206 B2   7/2009 Palti
(Continued)

FOREIGN PATENT DOCUMENTS

EP   1855757 A2   11/2007

OTHER PUBLICATIONS

Bomzon et al., "Modelling Tumor Treating Fields for the Treatment of Lung-Based Tumors", 2015 37th Annual International Conference of the IEEE Engineering in Medicine and Biology Society (Aug. 25-29, 2015), pp. 6888-6891.
(Continued)

*Primary Examiner* — Mallika D Fairchild
(74) *Attorney, Agent, or Firm* — Potomac Law Group, PLLC

(57) ABSTRACT

Tumors in portions of a subject's body that have a longitudinal axis (e.g., the torso, head, and arm) can be treated with TTFields by affixing first and second sets of electrodes at respective positions that are longitudinally prior to and subsequent to a target region. An AC voltage with a frequency of 100-500 kHz is applied between these sets of electrodes. This imposes an AC electric field with field lines that run through the target region longitudinally. The field strength is at least 1 V/cm in at least a portion of the target region. In some embodiments, this approach is combined with the application of AC electric fields through the target region in a lateral direction (e.g., front to back and/or side to side) in order to apply AC electric fields with different orientations to the target region.

20 Claims, 10 Drawing Sheets

Related U.S. Application Data

(60) Provisional application No. 62/356,986, filed on Jun. 30, 2016.

(51) Int. Cl.
    *A61N 1/32*     (2006.01)
    *A61K 41/00*     (2020.01)
    *A61B 18/00*     (2006.01)

(52) U.S. Cl.
    CPC ......... *A61N 1/0408* (2013.01); *A61N 1/0484* (2013.01); *A61N 1/0492* (2013.01); *A61N 1/321* (2013.01); *A61N 1/40* (2013.01); *A61B 2018/00059* (2013.01); *A61B 2018/00636* (2013.01)

(56) References Cited

U.S. PATENT DOCUMENTS

| | | | |
|---|---|---|---|
| 7,599,745 B2 | 10/2009 | Palti | |
| 7,706,890 B2 | 4/2010 | Palti | |
| 7,715,921 B2 | 5/2010 | Palti | |
| 8,244,345 B2 | 8/2012 | Palti | |
| 8,715,203 B2 | 5/2014 | Palti | |
| 2004/0176804 A1* | 9/2004 | Palti | A61N 1/326 607/2 |
| 2006/0276858 A1* | 12/2006 | Palti | A61N 1/32 607/76 |
| 2009/0048651 A1 | 2/2009 | Andino et al. | |
| 2011/0137229 A1* | 6/2011 | Palti | A61N 1/40 604/20 |
| 2012/0310303 A1 | 12/2012 | Popovic et al. | |

OTHER PUBLICATIONS

International Search Report and Written Opinion for International Application No. PCT/IB2017/053929 dated Nov. 24, 2017.

Kirson et al., "Alternating electric fields arrest cell proliferation in animal tumor models and human brain tumors", Proceedings of the National Academy of Sciences, Jun. 12, 2007, vol. 104(24), pp. 10152-10157.

* cited by examiner

ARRAYS FOR LONGITUDINAL DELIVERY OF TTFIELDS TO A BODY

CROSS REFERENCE TO RELATED APPLICATIONS

This application is a continuation of U.S. patent application Ser. No. 15/636,722, filed Jun. 29, 2017, which claims the benefit of U.S. Provisional Application 62/356,986 filed Jun. 30, 2016, each of which is incorporated herein by reference in their entirety.

BACKGROUND

Tumor Treating Fields (TTFields) are low intensity alternating electric fields (e.g., 1-3 V/cm) in the intermediate frequency range (e.g., 125-250 kHz, or in some cases 100-500 kHz) that target solid tumors by disrupting mitosis. TTFields are typically delivered through two pairs of electrode arrays. The electrode arrays that make up each of these pairs are positioned on opposite sides of the body part that is being treated. FIGS. 1A and 1B depict the conventional positioning of electrode arrays on a subject's head and thorax, respectively. In each of these examples, a first pair of electrode arrays includes one electrode array at an anterior position 16/19 and a second electrode array at a posterior position (not shown, but located directly behind the corresponding anterior position). When an AC voltage is applied between the anterior electrode array and the posterior electrode array, the field lines of the resulting electric field will run generally between the front and the back of the subject.

Each of the FIGS. 1A and 1B examples also includes a second pair of electrode arrays including one electrode array at a right-side position 14/17 and a second electrode array at a left-side position 15/18. When an AC voltage is applied between the right-side array and the left-side array, the field lines of the resulting electric field will run generally between the left and right sides of the subject. AC voltages are applied in an alternating sequence between (i) the anterior/posterior (A/P) electrode arrays and (ii) the right/left (R/L) electrode arrays so that the direction of the field will switch repeatedly (e.g., every 1 sec.) between the two directions described above.

While the A/P and R/L electrode arrays are well suited for applying electric fields in two roughly perpendicular directions into many portions of a subject's body, a number of situations can be envisioned in which A/P and R/L electrodes may be difficult or impossible to use. Examples include situations in which a subject has a sore or ulcer at one of the commonly-used sites for positioning an electrode array, as well as treating tumors at locations where using both A/P and R/L electrodes would be uncomfortable and/or impractical (e.g., in a subject's neck, elbow, knee, etc.).

SUMMARY OF THE INVENTION

One aspect of the invention is directed to a first apparatus for treating a target region in a subject's body with TTFields, the target region being located in a portion of the subject's body that has a longitudinal axis. This apparatus comprises a first set of one or more capacitively coupled electrodes and a first substrate configured to hold the first set of one or more electrodes against the subject's body so that the first set of one or more electrodes surrounds a first part of the subject's body at a position that is longitudinally prior to the target region. This apparatus also comprises a second set of one or more capacitively coupled electrodes and a second substrate configured to hold the second set of one or more electrodes against the subject's body so that the second set of one or more electrodes surrounds a second part of the subject's body at a position that is longitudinally subsequent to the target region. This apparatus also comprises a third set of one or more capacitively coupled electrodes and a third substrate configured to hold the third set of one or more electrodes against the subject's body on a first side of the target region, at a position that is longitudinally between the first set of one or more electrodes and the second set of one or more electrodes. This apparatus also comprises a fourth set of one or more capacitively coupled electrodes and a fourth substrate configured to hold the fourth set of one or more electrodes against the subject's body on a second side of the target region that is opposite to the first side, at a position that is longitudinally between the first set of one or more electrodes and the second set of one or more electrodes.

Some embodiments of the first apparatus further comprise an AC voltage generator configured to generate, in a repeating and alternating sequence, (a) an AC voltage with a frequency of 100-500 kHz between the first set of one or more electrodes and the second set of one or more electrodes, and (b) an AC voltage with a frequency of 100-500 kHz between the third set of one or more electrodes and the fourth set of one or more electrodes.

Some embodiments of the first apparatus further comprise an AC voltage generator configured to generate, in a repeating and alternating sequence, (a) an AC voltage with a frequency of 125-250 kHz between the first set of one or more electrodes and the second set of one or more electrodes, and (b) an AC voltage with a frequency of 125-250 kHz between the third set of one or more electrodes and the fourth set of one or more electrodes.

In some embodiments of the first apparatus, the first set of one or more electrodes comprises a first plurality of flat electrode elements, and the second set of one or more electrodes comprises a second plurality of flat electrode elements. In some of these embodiments, each of the first and second substrates is flexible.

In some embodiments of the first apparatus, each of the first and second substrates is shaped and dimensioned to fit around the subject's torso. In some embodiments of the first apparatus, the first substrate is shaped and dimensioned to fit around the subject's torso, and the second substrate is shaped and dimensioned to fit around the subject's neck. In some embodiments of the first apparatus, the first substrate is shaped and dimensioned to fit around the subject's neck, and the second substrate is shaped and dimensioned to fit around the subject's head. In some embodiments of the first apparatus, the first substrate is shaped and dimensioned to fit around the subject's neck, and the second substrate is shaped and dimensioned to fit on the subject's head. In some embodiments of the first apparatus, each of the first and second substrates is shaped and dimensioned to fit around the subject's limb.

Some embodiments of the first apparatus further comprise a fifth set of one or more capacitively coupled electrodes and a fifth substrate configured to hold the fifth set of one or more electrodes against the subject's body on a third side of the target region, at a position that is longitudinally between the first set of one or more electrodes and the second set of one or more electrodes. These embodiments also further comprise a sixth set of one or more capacitively coupled electrodes and a sixth substrate configured to hold the sixth set of one or more electrodes against the subject's body on a fourth side of the target region that is opposite to the third side, at a position that is longitudinally between the first set of one or more electrodes and the second set of one or more electrodes.

Another aspect of the invention is directed to a first method of treating a target region in a subject's body with TTFields, the target region being located in a portion of the subject's body that has a longitudinal axis. This method comprises affixing a first set of one or more electrodes to the subject's body so as to surround a first part of the subject's body at a position that is longitudinally prior to the target region; and affixing a second set of one or more electrodes to the subject's body so as to surround a second part of the subject's body at a position that is longitudinally subsequent to the target region. This method also comprises applying a first AC voltage with a frequency of 100-500 kHz between the first set of one or more electrodes and the second set of one or more electrodes so as to impose a first AC electric field with field lines that run through the target region longitudinally, the first AC electric field having a field strength of at least 1 V/cm in at least a portion of the target region.

In some embodiments of the first method, each of the first and second sets of one or more electrodes is capacitively coupled to the subject's body.

Some embodiments of the first method further comprise affixing a third set of one or more electrodes to the subject's body on a first side of the target region, at a position that is longitudinally between the first set of one or more electrodes and the second set of one or more electrodes, and affixing a fourth set of one or more electrodes to the subject's body on a second side of the target region that is opposite to the first side, at a position that is longitudinally between the first set of one or more electrodes and the second set of one or more electrodes. These methods also further comprise applying a second AC voltage with a frequency of 100-500 kHz between the third set of one or more electrodes and the fourth set of one or more electrodes so as to impose a second AC electric field through the target region, the second AC electric field having a field strength of at least 1 V/cm in at least a portion of the target region. In some of these embodiments, each of the first, second, third, and fourth sets of one or more electrodes is capacitively coupled to the subject's body. In some of these embodiments, each of the first and second AC voltages has a frequency of 125-250 kHz. In some of these embodiments, the steps of applying the first AC voltage and applying the second AC voltage are repeated at least 10,000 times in an alternating sequence.

Some embodiments of the first method further comprise affixing a fifth set of one or more electrodes to the subject's body on a third side of the target region, at a position that is longitudinally between the first set of one or more electrodes and the second set of one or more electrodes; and affixing a sixth set of one or more electrodes to the subject's body on a fourth side of the target region that is opposite to the third side, at a position that is longitudinally between the first set of one or more electrodes and the second set of one or more electrodes. These embodiments also further comprise applying a third AC voltage with a frequency of 100-500 kHz between the fifth set of one or more electrodes and the sixth set of one or more electrodes so as to impose a third AC electric field through the target region, the third AC electric field having a field strength of at least 1 V/cm in at least a portion of the target region. In some of these embodiments, the steps of applying the first AC voltage, applying the second AC voltage, and applying the third AC voltage are repeated at least 10,000 times in an alternating sequence.

In some embodiments of the first method, the first set of one or more electrodes comprises a first plurality of flat electrode elements distributed around the first part of the subject's body, and the second set of one or more electrodes comprises a second plurality of flat electrode elements distributed around the second part of the subject's body.

In some embodiments of the first method, the target region is located in the subject's torso, the first set of one or more electrodes is positioned around the subject's torso below the target region, and the second set of one or more electrodes is positioned around the subject's torso above the target region.

In some embodiments of the first method, the target region is located in the subject's torso, the first set of one or more electrodes is positioned around the subject's torso below the target region, and the second set of one or more electrodes is positioned around the subject's neck.

In some embodiments of the first method, the target region is located in the subject's head, the first set of one or more electrodes is positioned around the subject's neck, and the second set of one or more electrodes is positioned around the subject's head.

In some embodiments of the first method, the target region is located in the subject's limb. In these embodiments, the longitudinal axis runs through the limb in a proximal to distal direction, the first set of one or more electrodes is positioned around the limb at a position proximal to the target region, and the second set of one or more electrodes is positioned around the limb at a position distal to the target region.

Another aspect of the invention is directed to a second apparatus for treating a target region in a limb of a subject's body with TTFields. This apparatus comprises a first set of one or more capacitively coupled electrodes, and a first substrate configured to hold the first set of one or more electrodes against the subject's body so that the first set of one or more electrodes partially surrounds a first side of the limb at a position that is proximal to the target region. This apparatus also comprises a second set of one or more capacitively coupled electrodes, and a second substrate configured to hold the second set of one or more electrodes against the subject's body so that the second set of one or more electrodes partially surrounds a second side of the limb at a position that is distal to the target region. The second side of the limb is opposite to the first side of the limb. This apparatus also comprises a third set of one or more capacitively coupled electrodes, and a third substrate configured to hold the third set of one or more electrodes against the subject's body so that the third set of one or more electrodes partially surrounds the second side of the limb at a position that is proximal to the target region. This apparatus also comprises a fourth set of one or more capacitively coupled electrodes, and a fourth substrate configured to hold the fourth set of one or more electrodes against the subject's body so that the fourth set of one or more electrodes partially surrounds the first side of the limb at a position that is distal to the target region.

Some embodiments of the second apparatus further comprise an AC voltage generator configured to generate, in a repeating and alternating sequence, (a) a first AC voltage with a frequency of 100-500 kHz between the first set of one or more electrodes and the second set of one or more electrodes, and (b) a second AC voltage with a frequency of 100-500 kHz between the third set of one or more electrodes and the fourth set of one or more electrodes. In some of these embodiments, each of the first and second AC voltages has a frequency of 125-250 kHz.

In some embodiments of the second apparatus, each of the first, second, third, and fourth sets of one or more electrodes comprises a plurality of flat electrode elements. In some of these embodiments, each of the first, second, third, and fourth substrates is flexible.

In some embodiments of the second apparatus, the limb is an arm, each of the first and third substrates is shaped and dimensioned to fit on the arm proximally with respect to the elbow, and each of the second and fourth substrates is shaped and dimensioned to fit on the arm distally with respect to the elbow. In some embodiments of the second apparatus, the limb is a leg, each of the first and third substrates is shaped and dimensioned to fit on the leg proximally with respect to the knee, and each of the second and fourth substrates is shaped and dimensioned to fit on the leg distally with respect to the knee.

Another aspect of the invention is directed to a second method of treating a target region in a limb of a subject's body with TTFields. This method comprises affixing a first set of one or more electrodes so as to partially surround a first side of the limb at a position that is proximal to the target region, and affixing a second set of one or more electrodes so as to partially surround a second side of the limb at a position that is distal to the target region, wherein the second side of the limb is opposite to the first side of the limb. This method also comprises affixing a third set of one or more electrodes so as to partially surround the second side of the limb at a position that is proximal to the target region, and affixing a fourth set of one or more electrodes so as to partially surround the first side of the limb at a position that is distal to the target region. This method also comprises applying a first AC voltage with a frequency of 100-500 kHz between the first set of one or more electrodes and the second set of one or more electrodes so as to impose a first AC electric field through the target region, the first AC electric field having a field strength of at least 1 V/cm in at least a portion of the target region; and applying a second AC voltage with a frequency of 100-500 kHz between the third set of one or more electrodes and the fourth set of one or more electrodes so as to impose a second AC electric field through the target region, the second AC electric field having a field strength of at least 1 V/cm in at least a portion of the target region. In this method, the steps of applying the first AC voltage and applying the second AC voltage are performed in a repeating and alternating sequence.

In some embodiments of the second method, each of the first, second, third, and fourth sets of one or more electrodes is capacitively coupled to the subject's body. In some of these embodiments, each of the first and second AC voltages has a frequency of 125-250 kHz.

In some embodiments of the second method, the steps of applying the first AC voltage and applying the second AC voltage are repeated at least 10,000 times in an alternating sequence.

In some embodiments of the second method, the limb is an arm, the first set of one or more electrodes and the third set of one or more electrodes are positioned proximally with respect to the elbow, and the second set of one or more electrodes and the fourth set of one or more electrodes are positioned distally with respect to the elbow. In some embodiments of the second method, the limb is a leg, the first set of one or more electrodes and the third set of one or more electrodes are positioned proximally with respect to the knee, and the second set of one or more electrodes and the fourth set of one or more electrodes are positioned distally with respect to the knee.

In some embodiments of the second method, each of the first, second, third, and fourth sets of one or more electrodes comprises a plurality of flat electrode elements.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

The embodiments described below overcome the aforementioned limitations of using A/P and R/L electrodes by including at least one pair of electrode arrays configured to generate a longitudinal field in the target region. Note that as used herein: (1) in the context of the head and main portion of the body, the longitudinal axis is perpendicular to both the anterior-posterior axis and the lateral axis; (2) in the context of a leg or arm, the longitudinal axis is the proximal-distal axis; (3) the term "longitudinal field" refers to a field which runs in the same general direction as the longitudinal axis, and is not limited to fields that are exactly parallel to the longitudinal axis; (4) electrode arrays designed to generate longitudinal fields are referred to as "longitudinal arrays"; and (5) conventional electrode arrays designed to generate fields that run generally between either the left and right sides of the subject or the front and back of the subject are referred to as "latitudinal arrays."

To generate a longitudinal field, a pair of ring-shaped or arc-shaped electrode arrays that fit around the subject's body may be used, with one array positioned above the other. In some embodiments, the arrays are designed as rings that completely surround the body part on which they are placed. In other embodiments, the arrays are designed as arcs (e.g., semicircles) that partially surround the body part on which they are placed. When a voltage is applied between the upper and lower electrode arrays, the electric field that develops between them will be longitudinally oriented.

Figure 1A:
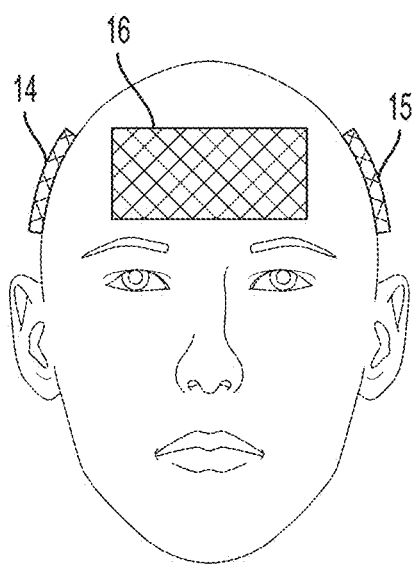
FIGS. 1A and 1B depict the conventional positioning of electrode arrays on a subject's head and thorax, respectively.
Figure 1B:
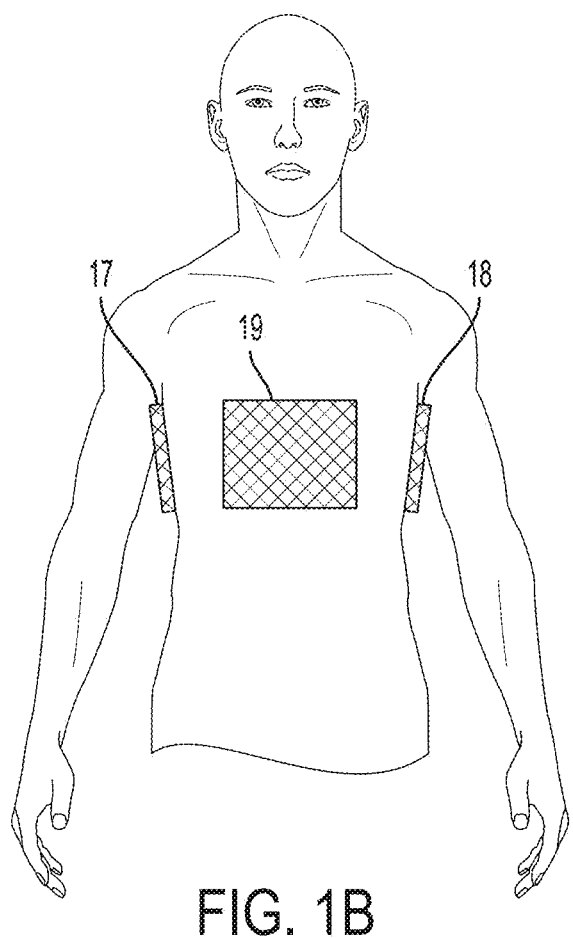
Figure 2:
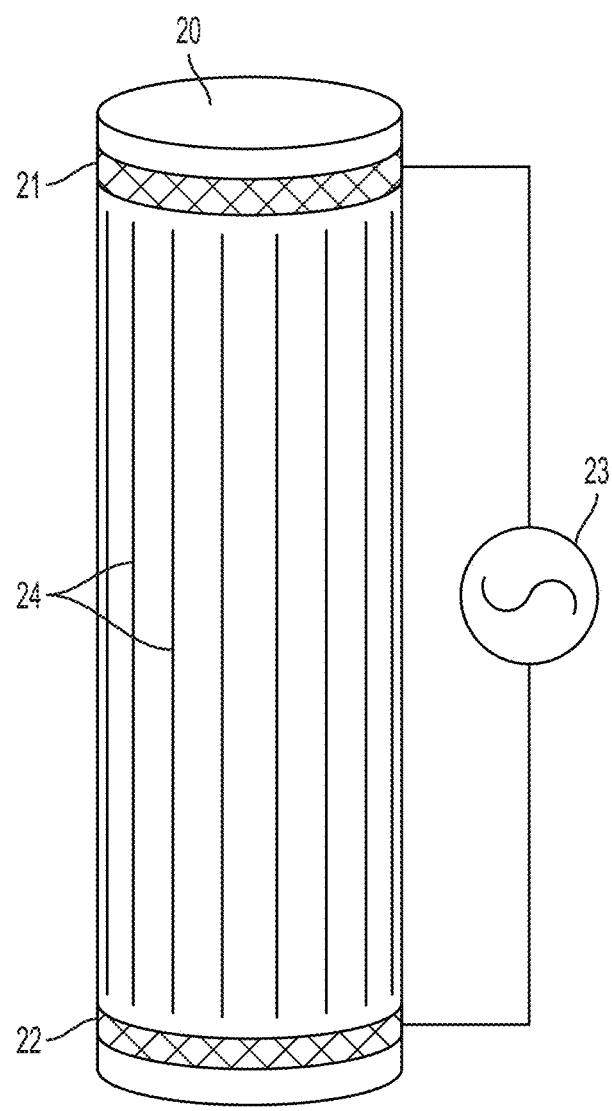
FIG. 2 is a schematic illustration depicting how longitudinal pairs of electrodes can be used to generate longitudinal electric fields in a cylindrical body.

FIG. 2 is a schematic illustration depicting a first order estimate of how longitudinal fields can be generated in the body. In this example, we consider the electric field in a solid conducting cylindrical body 20 when an AC voltage 25 is applied between thin ring-shaped electrode rings 21, 22 on either end of the cylinder 20. It turns out that the resulting electric field in the cylinder 20 will be almost uniformly directed longitudinally along the cylinder, as indicated by field lines 26, and will also penetrate into the interior of the cylinder 20. In some embodiments, the pair of electrode arrays for the delivery of TTFields may be designed as two ring-shaped arrays that fit around the subject's body, with one array placed above the other.

Using longitudinal fields can provide significant advantages because TTFields are more effective when they are parallel to the axis of cell division. As a result, increasing the number of directions at which the fields are applied can increase the effectiveness against the tumor that is being treated (in which the orientation of the cells during division can vary). Notably, the use of longitudinal arrays opens up new options for array layouts on the body that can optimize both field distribution and subject comfort.

FIGS. 3A-3D depict four examples of longitudinal pairs of electrode arrays designed to deliver TTFields to different parts of a person's body. In all of these embodiments, each of the electrode arrays includes one or more electrode elements mounted on a substrate that is configured to hold the electrode elements against the subject's body so that the electrode elements completely surround the respective body part. In some preferred embodiments, the substrate is flexible in order to promote conformance with the subject's body. An example of a suitable approach for mounting individual electrode elements on a flexible substrate is described below in connection with FIGS. 6A and 6B.

Figure 3A:
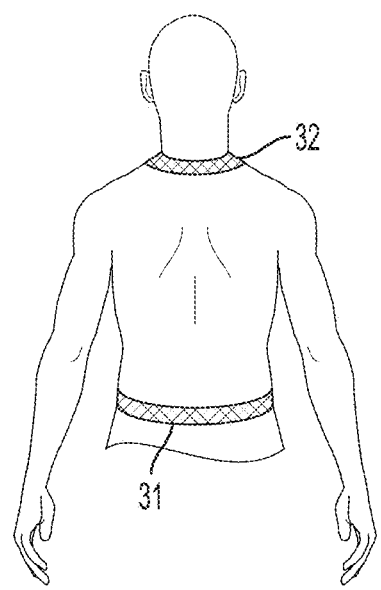
FIG. 3A depicts the positioning of longitudinal pairs of electrode arrays for delivering electric fields to the thorax or abdomen.
Figure 3B:
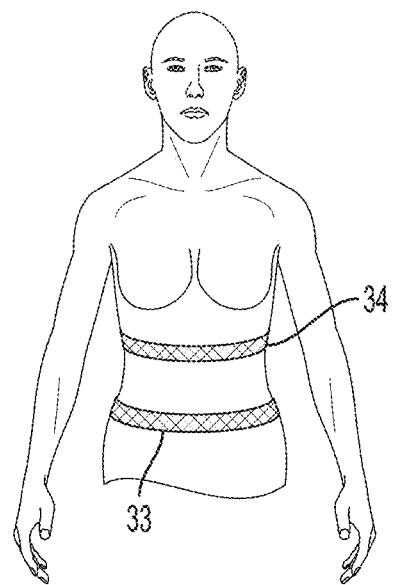
FIG. 3B depicts the positioning of longitudinal pairs of electrode arrays for delivering electric fields to the abdomen.

In the FIG. 3A embodiment, which is intended, e.g., for delivering fields to the thorax or abdomen, the first electrode array is placed at a position 31 around the torso (e.g., just above the subject's waist), and the second electrode array is placed at a position 32 around the subject's neck. In the FIG. 3B embodiment, which is intended, e.g., for delivering fields to the abdomen, the first electrode array is placed at a position 33 around the torso (e.g., just above the subject's waist), and the second electrode array is placed at a position 34 around the torso (e.g., at the top of the subject abdomen). In alternative embodiments (not shown), e.g., for delivering fields to the lungs, the first electrode array is placed below the chest (similar to position 34 in FIG. 3B) and the second electrode array is placed around the subject's neck (similar to position 32 in FIG. 3A.

Figure 3C:
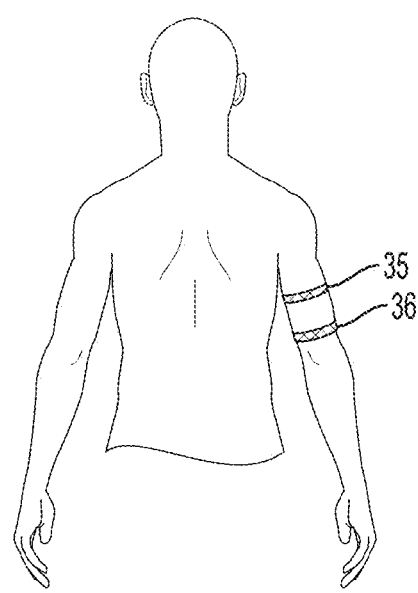
FIG. 3C depicts the positioning of longitudinal pairs of electrode arrays for delivering electric fields to a portion of the arm.

In the FIG. 3C embodiment, which is intended, e.g., for delivering fields to a portion of the arm, the first electrode array is placed at a position 35 on the arm that is proximal to the target region, and the second electrode array is placed at a position 36 on the arm that is distal to the target region. Target regions within the elbow can be accommodated by adjusting the location of these positions 35, 36. Similarly, in the FIG. 3D embodiment, which is intended, e.g., for delivering fields to a portion of the leg, the first electrode array is placed at a position 37 on the leg that is proximal to the target region, and the second electrode array is placed at a position 38 on the leg that is distal to the target region. Target regions within the knee can be accommodated by adjusting the location of these positions 37, 38.

Figure 3D:
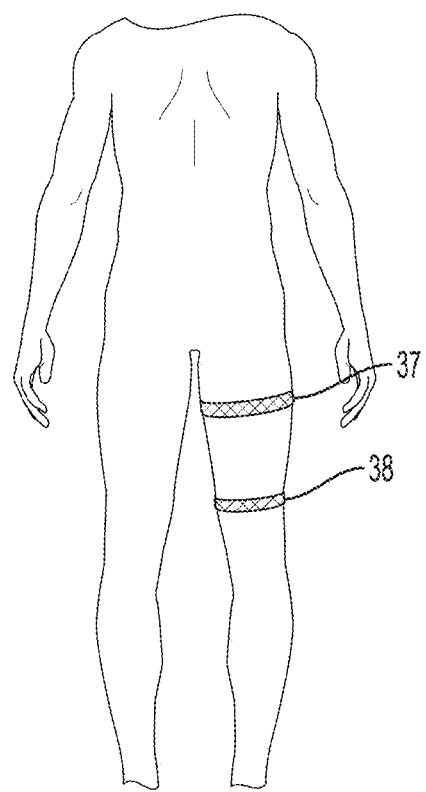
FIG. 3D depicts the positioning of longitudinal pairs of electrode arrays for delivering electric fields to a portion of the leg.
Figure 3E:
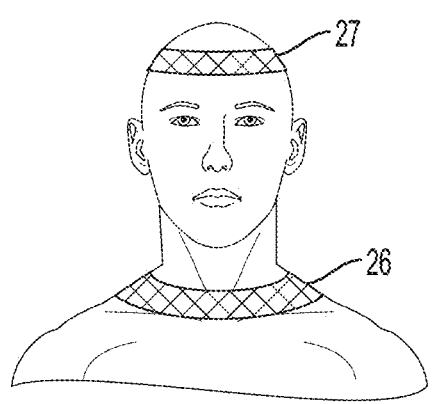
FIG. 3E depicts the positioning of longitudinal pairs of electrode arrays for delivering electric fields to the infratentorial brain, the brain stem, and to the neck.
Figure 3F:
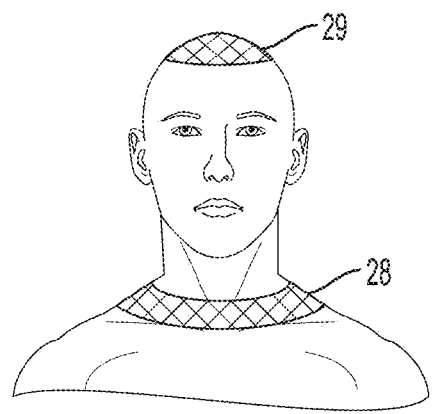
FIG. 3F depicts another embodiment for delivering electric fields to the infratentorial brain, the brain stem, and to the neck.

In the FIG. 3E embodiment, which is intended, e.g., for delivering TTFields to the infratentorial brain, the brain stem, and to the neck, the first electrode array is placed at a position 26 around the subject's neck, and the second electrode array is placed at a position 27 that is close to the crown of the subject's head. In the FIG. 3F embodiment, which is an alternative embodiment intended for delivering fields to these same anatomic locations, the first electrode array is placed at a position 28 around the subject's neck, and the second electrode array is placed at a position 29 on top of the subject's head.

Each of the embodiments depicted in FIGS. 3A-3E may be used for implementing a method of treating a target region in a subject's body with TTFields by (1) affixing a first set of one or more electrodes to the subject's body so as to surround a first part of the subject's body at a position that is longitudinally prior to the target region; (2) affixing a second set of one or more electrodes to the subject's body so as to surround a second part of the subject's body at a position that is longitudinally subsequent to the target region, and (3) applying a first AC voltage with a frequency of 100-500 kHz between the first set of one or more electrodes and the second set of one or more electrodes so as to impose a first AC electric field with field lines that run through the target region longitudinally, the first AC electric field having a field strength of at least 1 V/cm in at least a portion of the target region. In some preferred embodiments, the first and second sets of one or more electrodes our capacitively coupled to the subject body.

Depending on the anatomic location at which they are used, longitudinal arrays may provide one or more of the following advantages. First, longitudinal arrays may enable coverage of certain target regions with higher field intensities than latitudinal arrays. For instance, when treating lung tumors using only conventional latitudinal arrays, the arrays on the sides of the subject have to be positioned below the armpits. As a result, the field intensity in the upper lobes of the lungs is relatively low. In contrast, longitudinal arrays positioned around the waist and around the neck (as depicted in FIG. 3A) can provide a more uniform high field intensity throughout the lungs (as described below in connection with FIGS. 8 and 9A-9B).

Second, longitudinal arrays may adhere better to body contours than latitudinal arrays in certain anatomic locations. For example, when treating the thorax, latitudinal arrays placed on the chest may not adhere well to body contours (e.g., in the case of female breasts), leading to sub-optimal electric contact of the arrays and the body, reducing field intensity in the tumor. In these situations, the electric coupling of the field to the body through longitudinal arrays may provide better coverage than the electric coupling of the field to the body through latitudinal arrays.

Figure 4A:
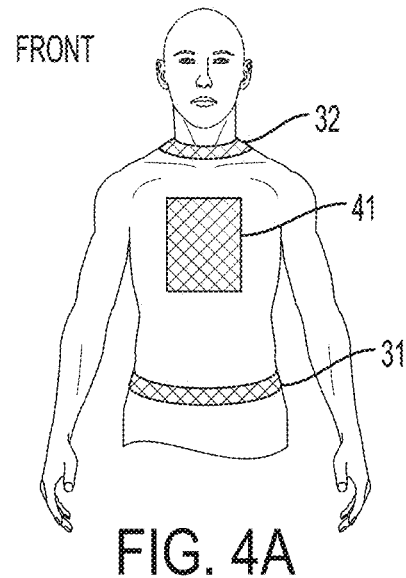
FIGS. 4A and 4B depict front and back views, respectively, of combining a pair of longitudinal arrays with a pair of anterior/posterior latitudinal arrays for delivering fields to the thorax or abdomen.
Figure 4B:
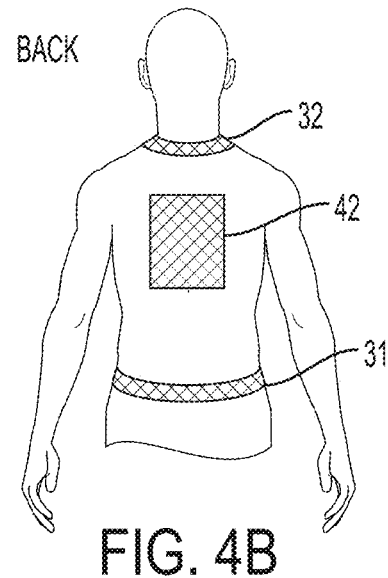

Third, large latitudinal arrays placed on the subject's body can limit motion or cause discomfort to the subject in certain anatomic locations. For example, when treating the thorax, large latitudinal arrays placed on the subject's chest (e.g., as depicted in FIGS. 4A-4B) may cause discomfort or even limit motion. In these cases, using a pair of properly designed longitudinal arrays (e.g., as depicted in FIG. 3A) to deliver the field can help to improve comfort, because a longitudinal pair of arrays, with one array circumventing the neck and one circumventing the upper abdomen or waist, can be more comfortable for the subject to use.

A fourth significant advantage is that the electric fields that are generated using longitudinal arrays are roughly perpendicular to the electric fields that are generated by latitudinal arrays (i.e., anterior-posterior or laterally-positioned sets of electrode arrays). Arrays designed to create longitudinal fields (e.g., as depicted in FIGS. 3A-3D) can therefore be combined with conventional arrays designed to create latitudinal fields in order to treat the target region with fields at a plurality of different directions, which can increase the efficacy of the treatment. The availability of longitudinal arrays also provides additional degrees of freedom for finding layouts for the electrodes that optimize field distribution and subject comfort.

FIGS. 4A-4H depict examples in which a pair of longitudinal arrays (e.g., similar to those described above in connection with FIGS. 3A-F) are combined with a pair of latitudinal arrays. In each of these situations, after the electrodes are affixed at their respective positions, (a) an AC voltage is applied between the first and second sets of electrodes that are arranged longitudinally in order to impose a longitudinal field in the target region, and (b) an AC voltage is applied between the third and fourth sets of electrodes that are arranged latitudinally in order to impose a latitudinal field in the target region. These steps (a) and (b) are repeated in an alternating sequence for the duration of the treatment, in order to repeatedly switch the direction of the field that is being imposed in the target region. In some embodiments, the switching rate is between 0.25 and 2 seconds. Because treatment preferably proceeds for many hours at a time, each of these steps (a) and (b) is preferably repeated at least 10,000 times. Preferably, the frequency of the AC voltages is between 100 and 500 kHz, and in some preferred embodiments, the frequency is between 125 and 250 kHz. In some preferred embodiments (e.g., for treating pancreatic cancer and certain types of lung cancer), the frequency is between 140 and 160 kHz. In some preferred embodiments (e.g., for treating ovarian cancer), the frequency is between 190 and 210 kHz. Preferably, each of the electric fields that is imposed in the target region has a field strength of at least 1 V/cm.

In the FIGS. 4A/B embodiment, which is intended, e.g., for delivering fields to the thorax, the longitudinal array is implemented with the first electrode array placed at a position 31 just above the subject's waist, and the second electrode array placed at a position 32 around the subject's neck. And in addition, a latitudinal array is provided with a third electrode array placed at a position 41 on the subject's chest, and a fourth electrode array placed at a position 42 on the subject's back. In this embodiment, the direction of the field lines of the latitudinal field will run from front to back.

Figure 4C:
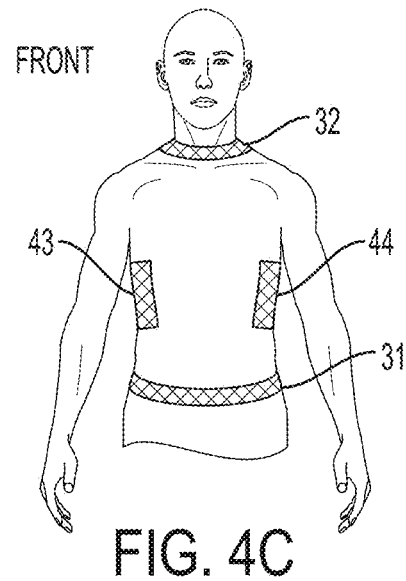
FIGS. 4C and 4D depict front and back views, respectively, of combining a pair of longitudinal arrays with a pair of left/right latitudinal arrays for delivering fields to the thorax or abdomen.
Figure 4D:
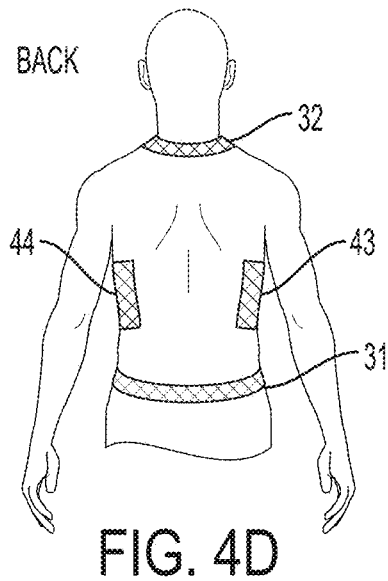

In the FIG. 4C/D embodiment, which is also intended, e.g., for delivering fields to the thorax, the longitudinal array is implemented in the same way as in FIGS. 4A/4B, but the latitudinal array is implemented with the third electrode array placed at a position 43 on the subject's right side, and the fourth electrode array placed at position 44 on the subject's left side. In this embodiment, the direction of the field lines of the latitudinal field will run from side to side.

Figure 4E:
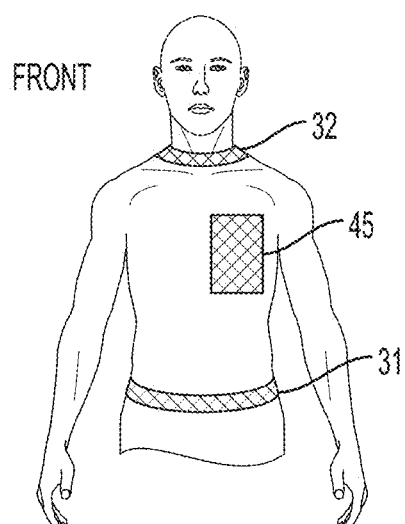
FIGS. 4E and 4F depict front and back views, respectively, of combining a pair of longitudinal arrays with a pair of diagonally positioned latitudinal arrays for delivering fields to the thorax.
Figure 4F:
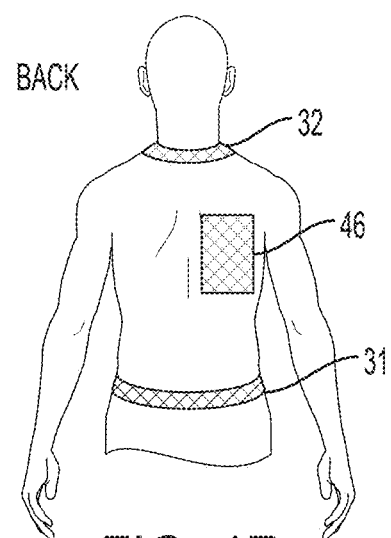

In the FIG. 4E/F embodiment, which is also intended, e.g., for delivering fields to the thorax, the longitudinal array is implemented in the same way as FIGS. 4A/4B, but the latitudinal array is implemented with the third electrode array placed at a position 45 on the left side of the subject's chest, and a fourth electrode array placed at position 46 on the right side of the subject's back. In this embodiment, the direction of the field lines of the latitudinal field will run diagonally through the subject's chest from front to back.

Figure 4G:
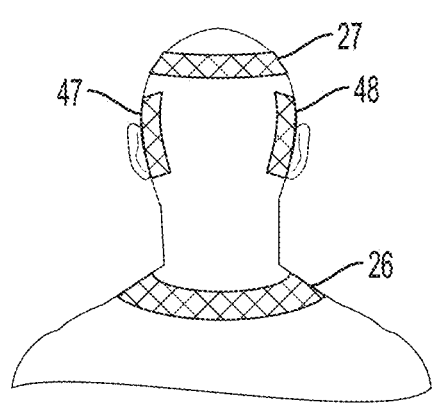
FIG. 4G depicts a rear view of combining a pair of longitudinal arrays with a pair of left/right latitudinal arrays for delivering fields to the infratentorial brain.

In the FIG. 4G embodiment, which is intended, e.g., for delivering TTFields to the infratentorial brain, the longitudinal array is implemented with the first electrode array placed at a position 26 around the subject's neck, and the second electrode array placed at a position 27 that is close to the crown of the subject's head. And in addition, a latitudinal array is provided with a third electrode array placed at a position 47 on the left side of the subject's head, and a fourth electrode array placed at position 48 on the right side of the subject's head. In this embodiment, the direction of the field lines of the latitudinal field will run from side to side. Alternatively, the latitudinal array may be provided using third and fourth electrodes (not shown) placed at positions on the front and back of the subject's head.

Figure 4H:
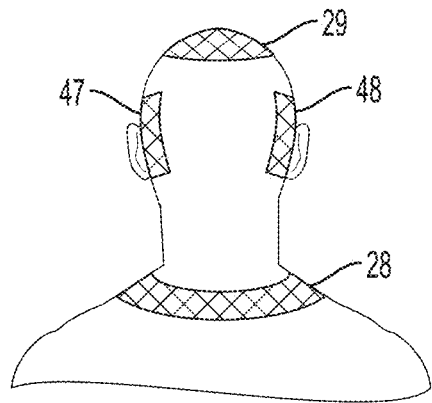
FIG. 4H depicts a rear view of another embodiment for combining longitudinal arrays with latitudinal arrays for use at the same anatomic locations as FIG. 4G.

The FIG. 4H embodiment is similar to the FIG. 4G embodiment, except that the longitudinal array is implemented with the first electrode array placed at a position 28 around the subject's neck, and the second electrode array placed at a position 29 on top of the subject's head.

Note that in addition to the embodiments described above in connection with FIGS. 4A-4H, a wide variety of alternative configurations that combine a pair of longitudinally positioned arrays with a pair of latitudinally positioned arrays can be readily envisioned for use at a wide range of anatomic locations, as will be apparent to persons skilled in the relevant arts.

FIGS. 5A-5D depict examples in which a pair of longitudinal arrays (e.g., similar to those described above in connection with FIGS. 3A-F) are combined with two pairs of latitudinal arrays. In each of these situations, (a) an AC voltage is applied between the first and second set of electrodes that are arranged longitudinally in order to impose a longitudinal field in the target region, (b) an AC voltage is applied between the third and fourth set of electrodes that are arranged latitudinally in order to impose a first latitudinal field in the target region; and (c) an AC voltage is applied between the fifth and sixth set of electrodes that are arranged latitudinally in order to impose a second latitudinal field in the target region. The angle between the first latitudinal field and the second latitudinal field is preferably between 60° and 120°, and most preferably as close as possible to 90°. These steps (a), (b), and (c) are repeated in an alternating sequence for the duration of the treatment, in order to repeatedly switch the direction of the field that is being imposed in the target region between each of the three directions. In some embodiments, the switching rate is between 0.25 and 2 seconds. Because treatment preferably proceeds for many hours at a time, each of these steps (a), (b), and (c) is preferably repeated at least 10,000 times.

Figure 5A:
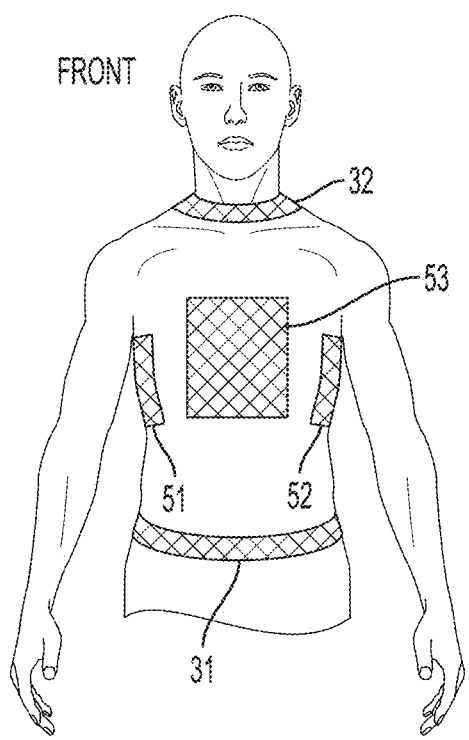
FIGS. 5A and 5B depict front and back views, respectively, of combining a pair of longitudinal arrays with both anterior/posterior latitudinal arrays and left/right latitudinal arrays for delivering fields to the thorax.
Figure 5B:
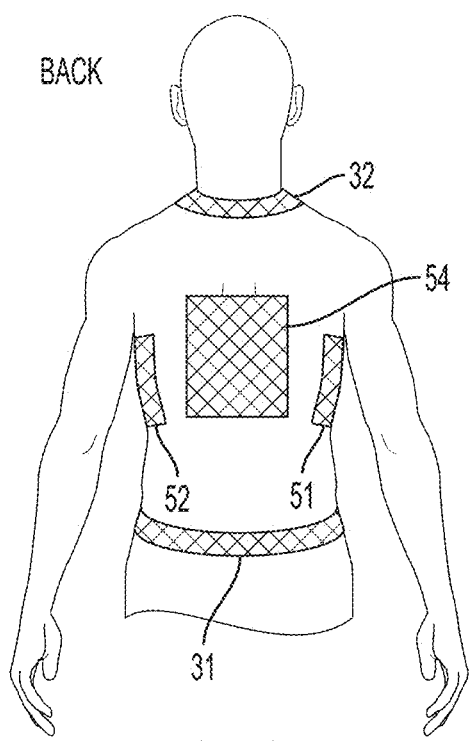

In the FIG. 5A/B embodiment, which is intended, e.g., for delivering fields to the thorax, the longitudinal array is implemented with the first electrode array placed at a position 31 just above the subject's waist, and the second electrode array placed at a position 32 around the subject's neck. In addition, a first latitudinal array is provided with a third electrode array placed at a position 41 on the subject's chest, and a fourth electrode array placed at a position 42 on the subject's back, in order to generate a first latitudinal field with field lines that run from front to back. Finally, a third latitudinal array is provided with a fifth electrode array placed at position 51 on the right side of the subject's body, and a sixth electrode array placed at position 52 on the left side of the subject body, in order to generate a second latitudinal field with field lines that run from side to side.

Figure 5C:
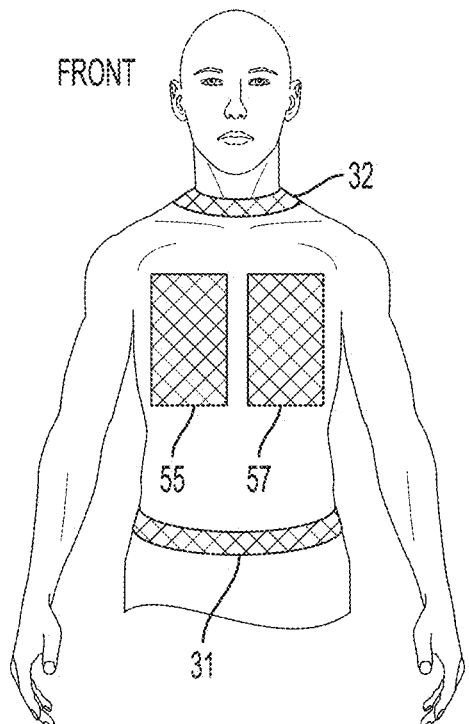
FIGS. 5C and 5D depict front and back views, respectively, of combining a pair of longitudinal arrays with two pairs of diagonally positioned latitudinal arrays for delivering fields to the thorax.
Figure 5D:
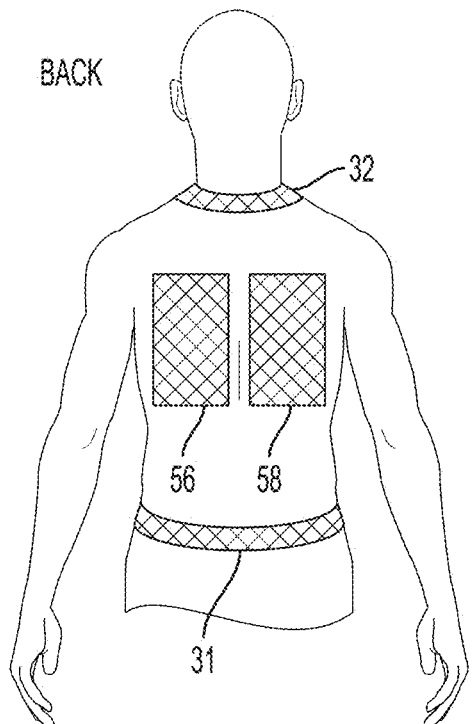

The FIG. 5C/D embodiment is similar to the FIG. 5A/B embodiment, except that the third and fourth electrode arrays are placed at positions 55 and 56 on the subject's front and back, respectively; and the fifth and sixth electrode arrays are placed at positions 57 and 58 on the subject's front and back, respectively. In this embodiment, the first latitudinal field will have field lines that run from the front right to the back left; and the second latitudinal field will have field lines that run from the front left to the back right. The angle between the first latitudinal field and the second latitudinal field is preferably between 60° and 120°, and most preferably as close as possible to 90°.

Here again, in addition to the two embodiments described above in connection with FIGS. 5A-5D, a wide variety of alternative configurations that combine a pair of longitudinally positioned arrays with two pairs of latitudinally positioned arrays can be readily envisioned for use at a wide range of anatomic locations, as will be apparent to persons skilled in the relevant arts.

The discussion of FIGS. 3-5 above explains the positions at which the various sets of electrodes are placed on the subject's body, but do not describe the construction of those sets of electrodes. A wide variety of construction for implementing those sets of electrodes may be used, including but not limited to the configurations depicted in FIGS. 6A and 6B.

Figure 6A:
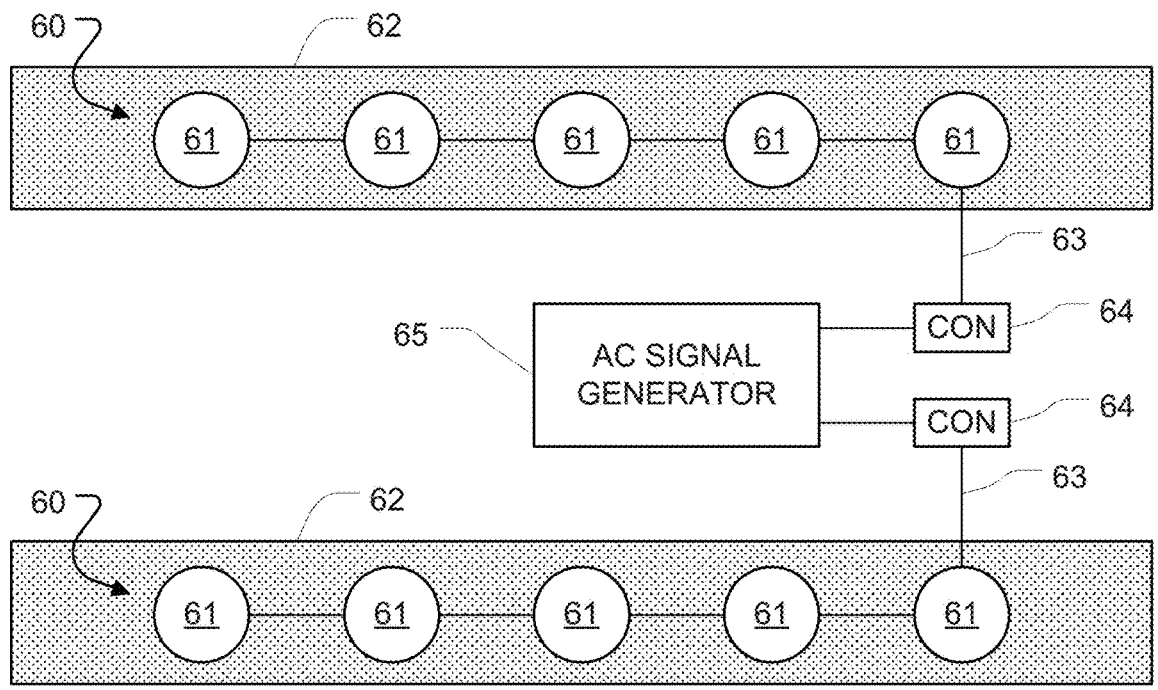
FIG. 6A depicts a first configuration that is suitable for affixing a band or belt-shaped set of electrodes to a subject's body.

FIG. 6A depicts a first configuration that is suitable for affixing a set of electrodes 60 to a subject's body. In this embodiment, each set of electrodes 60 includes a plurality of individual electrode elements 61 mounted on a band-shaped substrate 62. The band-shaped substrate 62 is shaped and dimensioned to fit on the particular body part where it will be used. For example, for the longitudinal array depicted at position 31 in FIG. 3A, the substrate 62 will be a flexible substrate that resembles a belt; for the longitudinal array depicted at position 32 in FIG. 3A, the substrate 62 would be a flexible substrate that resembles a choker; and for the longitudinal array depicted at position 27 in FIG. 3E, the substrate 62 would be a flexible substrate that resembles a headband, etc. The job of the substrate 62 is to hold the individual electrode elements 61 against the subject's skin so that those elements make good contact the skin. Optionally, conductive gel may be applied between the electrode elements 61 and the subject's skin.

In some embodiments, each of the individual electrode elements 61 is a disk-shaped capacitively coupled electrode with a high dielectric constant, such as the electrode elements used in the conventional Novocure TTF-100L transducer arrays. In alternative embodiments, instead of using a plurality of individual electrode elements 61, a single electrode element (not shown) may be used, in which case the single electrode element is preferably either flexible or contoured to conform with the particular portion of the subject's body where it will be used.

The individual electrode elements 61 within each set of electrodes 60 are wired together using appropriate wiring 63. For example, the individual electrode elements 61 may be wired in parallel, in series, or in a parallel/series combination. Optionally, this wiring 63 may terminate at a connector 64. This connector 64 may be used to connect the set of electrodes 60 with the AC signal generator 65, so that the AC signal generator 65 can apply a voltage between two sets of electrodes.

Figure 6B:
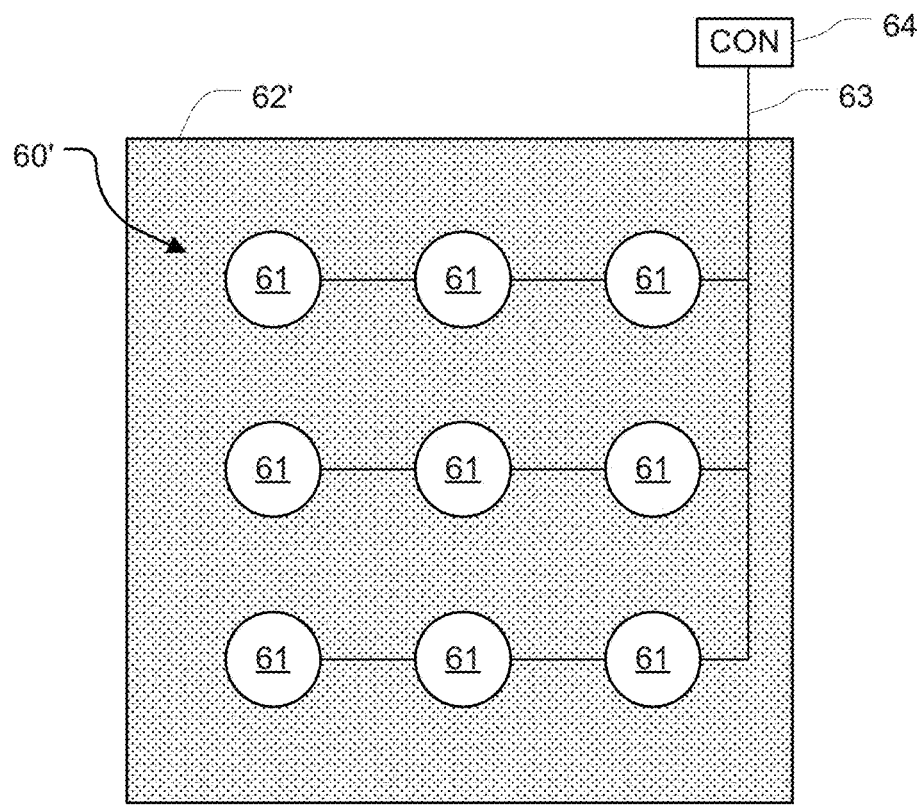
FIG. 6B depicts a second configuration that is suitable for affixing a panel-shaped set of electrodes to a subject's body.

FIG. 6B depicts a second configuration that is suitable for affixing a panel-shaped set of electrodes 60' to a subject's body. This configuration includes a plurality of individual electrode elements 61 mounted on a panel-shaped substrate 62'. The wiring 63 and connector 64 in this FIG. 6B embodiment is similar to the corresponding elements in FIG. 6A. This FIG. 6B embodiment is best suited for placement at locations 41-58 (depicted in FIGS. 4-5) and for generating the lateral fields described above in connection with those embodiments.

A wide variety of alternative substrate configurations for mounting a plurality of individual electrode elements will be apparent to persons skilled in the relevant arts, based on the anatomical position at which the electrode elements are positioned. FIGS. 7A-F depict the positioning of the electrode elements in three such configurations. The substrate that supports the electrode elements for the longitudinal sets of electrodes 71, 72 shown in FIGS. 7A/B (which depict front and back views, respectively) will be similar to the band-shaped configuration shown in FIG. 6A, scaled to the appropriate size for the relevant anatomy. The substrate that supports the electrode elements for the anterior/posterior latitudinal sets of electrodes 73/74 depicted in FIGS. 7C/D (which depict front and back views, respectively) and for the right/left latitudinal sets of electrodes 75/76 depicted in FIGS. 7E/F (which depict front and back views, respectively), will be similar to the panel-shaped configurations shown in FIG. 6B, scaled and shaped to the appropriate size for the relevant anatomy. Combining all three of the electrode configurations FIGS. 7A/B, 7C/D, and 7E/F and cycling the field between those three pairs of electrodes to provide three different field directions can provide excellent field coverage of the upper lobes of the lungs while maintaining patient comfort.

Figure 7A:
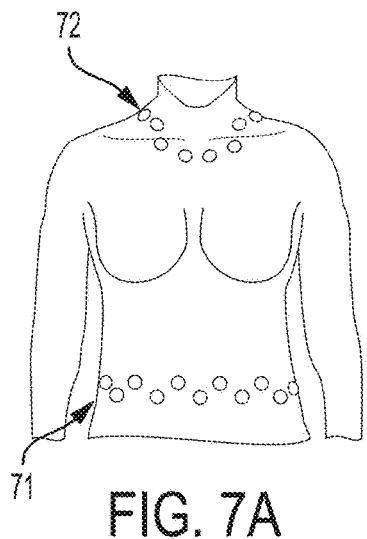
FIGS. 7A and 7B depict front and back views, respectively of the positioning of a plurality of electrode elements for one example of a pair of longitudinal arrays.
Figure 7C:
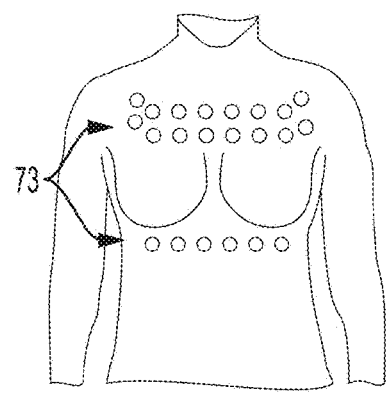
FIGS. 7C and 7D depict front and back views, respectively of the positioning of a plurality of electrode elements for one example of a pair of anterior/posterior latitudinal arrays.
Figure 7E:
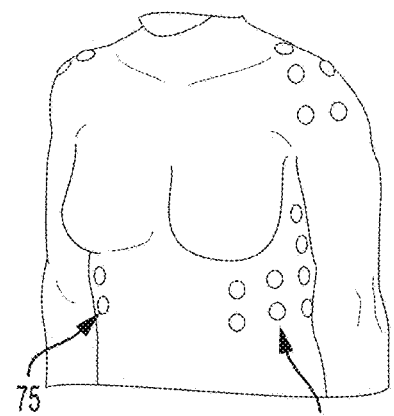
FIGS. 7E and 7F depict front and back views, respectively of the positioning of a plurality of electrode elements for one example of a pair of left/right latitudinal arrays.
Figure 7B:
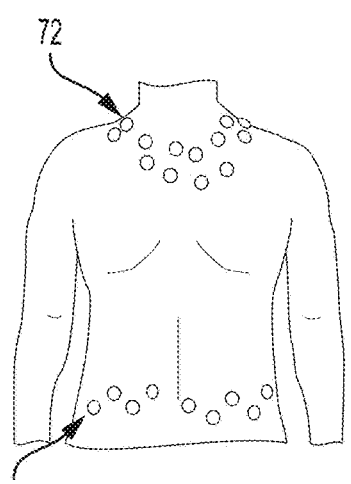
Figure 7D:
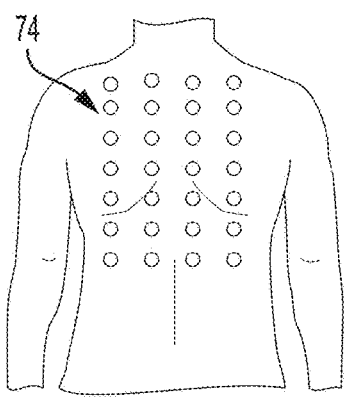
Figure 7F:
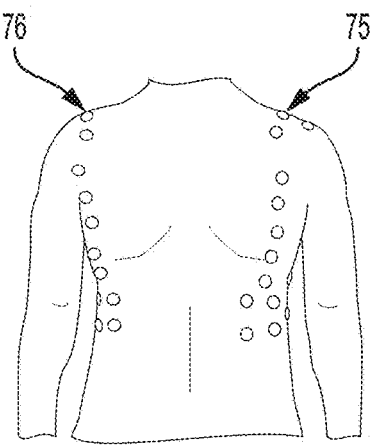

Finite element method calculations reveal that longitudinal arrays can provide effective penetration of relevant anatomical structures. In one example, a plurality of ceramic disk-shaped electrode elements is distributed at a first position 71 that corresponds to the waist and a second position 72 that corresponds to the neck of a realistic computational phantom as depicted in FIGS. 7A/B.

Figure 8:
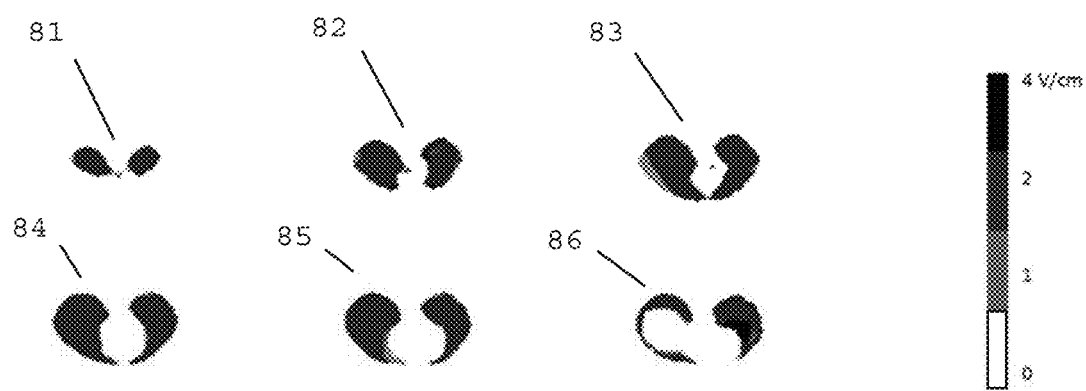
FIG. 8 depicts the strength of the electric field for six axial slices using the FIG. 7A/B positioning, as calculated using a finite element simulation.
Figure 9A:
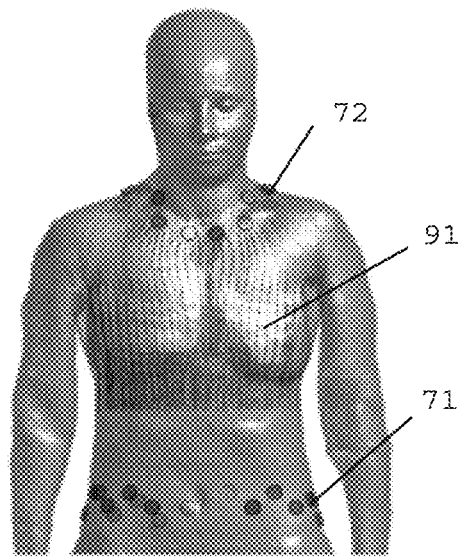
FIGS. 9A and 9B depict the directions of the field lines of the longitudinal field through the body and the lungs, respectively, for the FIG. 7A/B positioning.
Figure 9B:
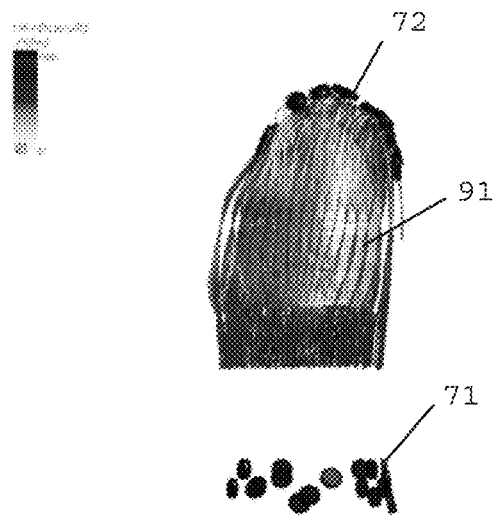

FIG. 8 depicts the strength of the electric field for this example, as calculated using a finite element simulation, for axial slices 81-86 spaced at regular vertical intervals through the lungs. This simulation reveals that it is possible to obtain field intensities between 1-4 V/cm field intensities throughout most of the lungs using longitudinal arrays. FIGS. 9A/B depict the directions 91 of the field lines of the longitudinal field through the body and the lungs, respectively, for this simulation. These figures show the longitudinal nature of those field lines.

In some cases, using at least one pair of longitudinal arrays may be the only practical way to treat a tumor using TTFields. For instance, if a tumor is located in a joint such as the knee or elbow, using only lateral sets of electrodes could significantly hamper the subject's mobility.

Figures 10A, 10B:
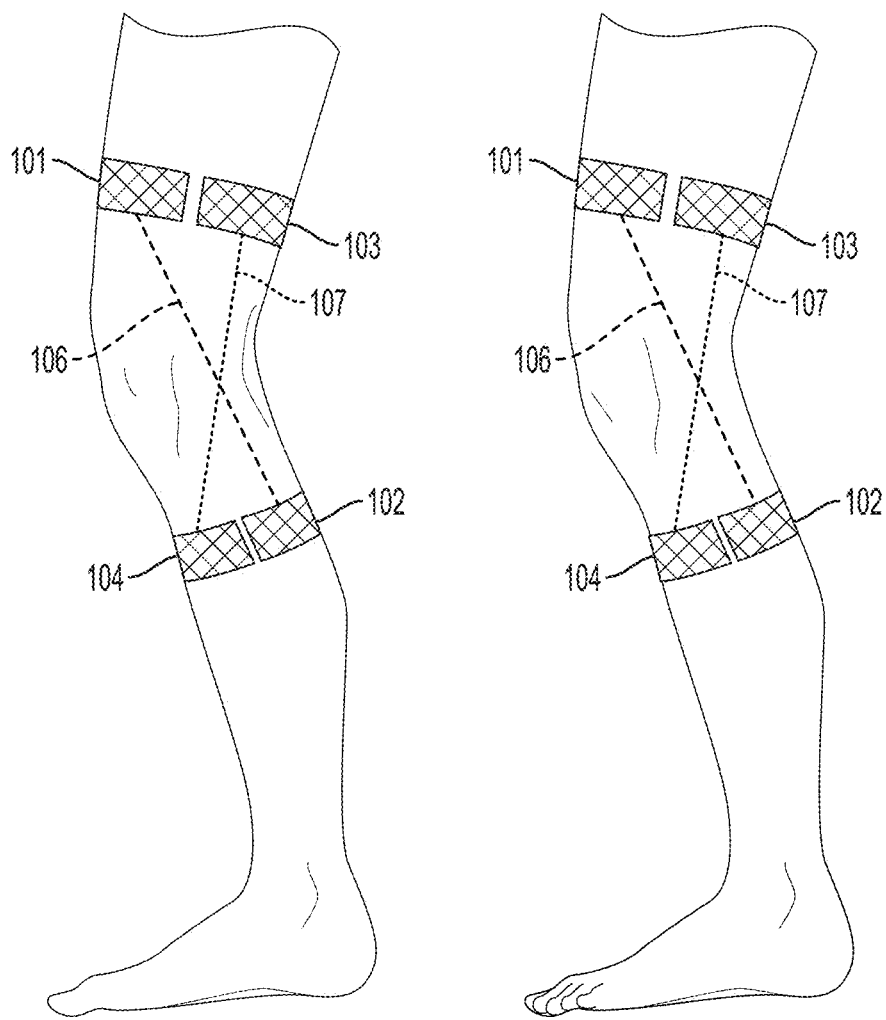
FIGS. 10A and 10B depict inner and outer views, respectively, of an embodiment intended for delivering fields to a knee using two pairs of longitudinal arrays.

FIGS. 10A and 10B depict inner and outer views, respectively, of an embodiment intended for delivering fields to a knee using two pairs of longitudinal arrays, which overcomes this mobility problem. In this embodiment, a first substrate holds a first set of one or more electrodes against the leg so that it partially surrounds the front side of the leg at a position 101 that is proximal to the knee, a second substrate holds a second set of one or more electrodes against the leg so that it partially surrounds the back side of the leg at a position 102 that is distal to the knee, a third substrate holds a third set of one or more electrodes against the leg so that it partially surrounds the back side of the leg at a position 103 that is proximal to the knee, and a fourth substrate holds a fourth set of one or more electrodes against the leg so it partially surrounds the front side of the leg at a position 104 that is distal to the knee.

Each set of electrodes at positions 101-104 is preferably shaped like an open arc that conform with the contours of the leg. This arc shape may be achieved using flexible substrates upon which a plurality of individual electrode elements are mounted, as described above in connection with FIG. 6A. Alternatively, the arc shape may be achieved using a rigid substrate upon which one or more electrode elements are mounted. When the open arc configuration is used for the electrode arrays, it is important to place the arrays in any given pair on opposite aspects of the body part being used to ensure that the field penetrates the body, because if both arcs in a given electrode pair are placed on the same aspect on the body, then a significant electric field may only develop in the superficial regions of the body.

In this embodiment, a first AC voltage is applied between the set of electrodes affixed at position 101 and the set of electrodes affixed at position 102, resulting in an electric field with field lines that run in the general direction of the dashed line 106. Subsequently, a second AC voltage is applied between the set of electrodes affixed at position 103 and the set of electrodes affixed at position 104, resulting in an electric field with field lines that run in the general direction of the dotted line 107. This configuration would result in two electric fields that form an X-shape through the joint. Although the directions of these two fields (106, 107) may not be perpendicular, the angle between those fields will be sufficiently large to provide improved results with respect to a single-direction field. Preferably, the frequency of the first and second AC voltages is between 100 and 500 kHz.

In some preferred embodiments, this frequency is between 125 and 250 kHz. Preferably, the strength of the two electric fields is at least 1 V/cm in at least a portion of the target region.

In alternative embodiments, a knee may be treated by combining one pair of longitudinal arrays positioned above and below the joint with one pair of latitudinal arrays placed on the lateral sides of the joint. In these embodiments, the longitudinal arrays may completely surround the leg (e.g., as seen in FIG. 3D) or may partially surround the leg (e.g., as described above in connection with FIG. 10).

Note that the same concepts described above in connection with FIG. 10 in the context of a knee can also be applied in the context of an elbow or to other joints if appropriate changes to the relevant dimensions are made.

Note that in some cases (e.g., the FIG. 3A-3F embodiments), the arrays are designed to completely circumvent the body part on which they are placed, and in other cases (e.g., the FIG. 10A-B embodiments), the arrays are designed as open arcs that do not completely circumvent the body part on which they are is placed. But in both of those array configurations, each of the arrays must be positioned at a different position along the longitudinal axis.

TTFields may be delivered through electrode arrays that capacitively couple the electric field generated by a field generating device into the body. For instance, the array design structure described in U.S. Pat. No. 7,715,921, could be incorporated into the design of longitudinal arrays. The electrode arrays could also be designed as a composite electrode comprising a plurality of ceramic elements that are designed to be positioned against the subject's skin as described in U.S. Pat. No. 8,715,203.

In some embodiments, the arrays are designed as a set of ceramic disks with a high dielectric constant which are connected to the body via a thin conductive gel. The disks in each array are electrically inter-connected via a flex wire, and an adhesive tape is placed above the disks so that the array adheres firmly to the subject's body. The components for creating the longitudinal arrays may be similar to those that are currently used to deliver TTFields to the head using Optune™, as well as to deliver TTFields to the torso using the NovoTTF-100L. The ceramic elements can be wired in parallel, in series, or in any combination of parallel and series (e.g., 3 groups wired in parallel, where each group includes 3 disks wired in series).

Optionally, the design of the array layout could be performed with the assistance of finite element simulations, which could be used to calculate the expected field distribution that any specific design of longitudinal arrays will yield. Such designs may be optimized to deliver a maximal field intensity to a target region.

Optionally, the disks in each array may be connected in a manner that enables them to be fitted to subjects of different sizes (e.g., each array may comprise several connected patches with a small number of disks, or the disks may be connected with flexible connectors).

While the above embodiments are described in the context of a human subject, they may also be used for other animals (e.g., dogs, horses, etc.) by making appropriate modifications, which will be apparent to persons skilled in the relevant arts.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A kit of electrodes for treating a target region in a subject's body with Tumor Treating Fields (TTFields), the target region being located in a portion of the subject's body that has a longitudinal axis, the kit comprising:
   a first plurality of capacitively coupled electrodes wired together in parallel, in series, or in a parallel/series combination;
   a first band-shaped substrate configured to hold the first plurality of electrodes against the subject's body so that the first plurality of electrodes surrounds a first part of the subject's body at a position that is longitudinally prior to the target region;
   a second plurality of capacitively coupled electrodes wired together in parallel, in series, or in a parallel/series combination;
   a second band-shaped substrate configured to hold the second plurality of electrodes against the subject's body so that the second plurality of electrodes surrounds a second part of the subject's body at a position that is longitudinally subsequent to the target region;
   a third plurality of capacitively coupled electrodes wired together in parallel, in series, or in a parallel/series combination;
   a third substrate configured to hold the third plurality of electrodes against the subject's body on a first side of the target region, at a position that is longitudinally between the first plurality of electrodes and the second plurality of electrodes;
   a fourth plurality of capacitively coupled electrodes wired together in parallel, in series, or in a parallel/series combination; and
   a fourth substrate configured to hold the fourth plurality of electrodes against the subject's body on a second side of the target region that is opposite to the first side, at a position that is longitudinally between the first plurality of electrodes and the second plurality of electrodes.

2. The kit of claim 1, further comprising an AC voltage generator configured to generate, in a repeating and alternating sequence, (a) an AC voltage with a frequency of 100-500 kHz between the first plurality of electrodes and the second plurality of electrodes, and (b) an AC voltage with a frequency of 100-500 kHz between the third plurality of electrodes and the fourth plurality of electrodes.

3. The kit of claim 1, further comprising an AC voltage generator configured to generate, in a repeating and alternating sequence, (a) an AC voltage with a frequency of 125-250 kHz between the first plurality of electrodes and the second plurality of electrodes, and (b) an AC voltage with a frequency of 125-250 kHz between the third plurality of electrodes and the fourth plurality of electrodes.

4. The kit of claim 1, wherein the first plurality of electrodes are all wired together in parallel, and the second plurality of electrodes are all wired together in parallel.

5. The kit of claim 4, wherein each of the first and second substrates is flexible.

6. The kit of claim 1, wherein each of the first and second substrates is shaped and dimensioned to fit around a torso of the subject's body.

7. The kit of claim 1, wherein the first substrate is shaped and dimensioned to fit around a torso of the subject's body, and wherein the second substrate is shaped and dimensioned to fit around a neck of the subject's body.

8. The kit of claim 1, wherein the first substrate is shaped and dimensioned to fit around a neck of the subject's body, and wherein the second substrate is shaped and dimensioned to fit around a head of the subject's body.

9. The kit of claim 1, wherein the first substrate is shaped and dimensioned to fit around a neck of the subject's body, and wherein the second substrate is shaped and dimensioned to fit on a head of the subject's body.

10. The kit of claim 1, wherein each of the first and second substrates is shaped and dimensioned to fit around a limb of the subject's body.

11. The kit of claim 1, further comprising:
   a fifth plurality of capacitively coupled electrodes;
   a fifth substrate configured to hold the fifth plurality of electrodes against the subject's body on a third side of the target region, at a position that is longitudinally between the first plurality of electrodes and the second plurality of electrodes;
   a sixth plurality of capacitively coupled electrodes; and
   a sixth substrate configured to hold the sixth plurality of electrodes against the subject's body on a fourth side of the target region that is opposite to the third side, at a position that is longitudinally between the first plurality of electrodes and the second plurality of electrodes.

12. A kit of electrodes for treating a target region in a subject's body with Tumor Treating Fields (TTFields), the target region being located in a portion of the subject's body that has a longitudinal axis, the kit comprising:
   a first plurality of capacitively coupled electrodes wired together in parallel, in series, or in a parallel/series combination;
   a first band-shaped substrate configured to hold the first plurality of electrodes against the subject's body so that the first plurality of electrodes surrounds a first part of the subject's body at a position that is longitudinally prior to the target region;
   a second plurality of capacitively coupled electrodes wired together in parallel, in series, or in a parallel/series combination; and
   a second band-shaped substrate configured to hold the second plurality of electrodes against the subject's body so that the second plurality of electrodes surrounds a second part of the subject's body at a position that is longitudinally subsequent to the target region.

13. The kit of claim 12, further comprising an AC voltage generator configured to impose an AC voltage with a frequency of 100-500 kHz between the first plurality of electrodes and the second plurality of electrodes.

14. The kit of claim 12, further comprising an AC voltage generator configured to impose an AC voltage with a frequency of 125-250 kHz between the first plurality of electrodes and the second plurality of electrodes.

15. The kit of claim 12, wherein the first plurality of electrodes are all wired together in parallel, and the second plurality of electrodes are all wired together in parallel, and wherein each of the first and second substrates is flexible.

16. The kit of claim 12, wherein each of the first and second substrates is shaped and dimensioned to fit around a torso of the subject's body.

17. The kit of claim 12, wherein the first substrate is shaped and dimensioned to fit around a torso of the subject's body, and wherein the second substrate is shaped and dimensioned to fit around a neck of the subject's body.

18. The kit of claim 12, wherein the first substrate is shaped and dimensioned to fit around a neck of the subject's body, and wherein the second substrate is shaped and dimensioned to fit around a head of the subject's body.

19. The kit of claim 12, wherein the first substrate is shaped and dimensioned to fit around a neck of the subject's body, and wherein the second substrate is shaped and dimensioned to fit on a head of the subject's body.

20. The kit of claim 12, wherein each of the first and second substrates is shaped and dimensioned to fit around a limb of the subject's body.

\* \* \* \* \*